United States Patent
Kohle et al.

(10) Patent No.: US 10,748,315 B2
(45) Date of Patent: Aug. 18, 2020

(54) CONTROL METHOD FOR A MEDICAL IMAGING SYSTEM

(71) Applicant: Siemens Healthcare GmbH, Erlangen (DE)

(72) Inventors: Sven Kohle, Erlangen (DE); Andreas Prause, Nuremberg (DE); Maria Kroell, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 149 days.

(21) Appl. No.: 15/950,565

(22) Filed: Apr. 11, 2018

(65) Prior Publication Data

US 2018/0293773 A1 Oct. 11, 2018

(30) Foreign Application Priority Data

Apr. 11, 2017 (EP) .................... 17166063

(51) Int. Cl.
| | |
|---|---|
| *G06K 9/00* | (2006.01) |
| *G06T 11/60* | (2006.01) |
| *G06K 9/62* | (2006.01) |
| *G16H 30/20* | (2018.01) |
| *A61B 5/055* | (2006.01) |
| *A61B 6/03* | (2006.01) |
| *G16H 40/63* | (2018.01) |

(Continued)

(52) U.S. Cl.
CPC .............. *G06T 11/60* (2013.01); *A61B 5/055* (2013.01); *A61B 6/032* (2013.01); *A61B 6/463* (2013.01); *A61B 6/5211* (2013.01); *G06K 9/6215* (2013.01); *G16H 30/20* (2018.01); *G16H 30/40* (2018.01); *G16H 40/63* (2018.01); *G16H 50/50* (2018.01); *A61B 6/467* (2013.01); *A61B 6/56* (2013.01); *G06F 3/0486* (2013.01); *G06F 3/04845* (2013.01); *G06T 2200/24* (2013.01); *G06T 2210/41* (2013.01)

(58) Field of Classification Search
CPC . G06T 11/60; G06T 2200/24; G06T 2210/41; G16H 50/50; G16H 30/20; G16H 30/40; G16H 40/63; A61B 5/055; A61B 6/032; A61B 6/463; A61B 6/5211; A61B 6/467; A61B 6/56; G06K 9/6215; G06F 3/04845; G06F 3/0486
See application file for complete search history.

(56) References Cited

U.S. PATENT DOCUMENTS 9,026,217 B2 * 5/2015 Kokones ............ A61N 1/37247
607/45
10,070,839 B2 * 9/2018 Westerhoff ............. A61B 6/025
(Continued)

OTHER PUBLICATIONS

European Action dated Jun. 10, 2020, for Application No. 17 166 063.2.

*Primary Examiner* — Shefali D Goradia
(74) *Attorney, Agent, or Firm* — Schiff Hardin LLP

(57) ABSTRACT

In a control method for a screen display of a medical imaging system, an image data set of a patient is acquired and a comparison of the acquired image data set is made with a number of pre-stored image data sets, each of which is stored with layout parameters for the screen display associated therewith. Display of the acquired image data set take place with the layout parameters of the pre-stored image data set that has the greatest similarity with the acquired image data set.

20 Claims, 4 Drawing Sheets

(51) Int. Cl.
*A61B 6/00* (2006.01)
*G16H 30/40* (2018.01)
*G16H 50/50* (2018.01)
G06F 3/0486 (2013.01)
G06F 3/0484 (2013.01)

(56) References Cited

U.S. PATENT DOCUMENTS

| | | | |
|---|---|---|---|
| 2005/0110748 A1* | 5/2005 | Boeing | A61B 6/032 |
| | | | 345/156 |
| 2007/0265813 A1* | 11/2007 | Unal | G06T 7/0012 |
| | | | 703/2 |
| 2009/0094513 A1 | 4/2009 | Bay | |
| 2009/0254566 A1* | 10/2009 | Bay | G06F 19/00 |
| 2010/0100560 A1 | 4/2010 | Bystrov et al. | |
| 2013/0129198 A1* | 5/2013 | Sherman | G06F 19/321 |
| | | | 382/159 |
| 2014/0143710 A1 | 5/2014 | Zhao et al. | |
| 2015/0051480 A1* | 2/2015 | Hwang | A61B 8/08 |
| | | | 600/424 |
| 2015/0170362 A1* | 6/2015 | Kroell | G16H 40/63 |
| | | | 382/132 |

\* cited by examiner

CONTROL METHOD FOR A MEDICAL IMAGING SYSTEM

BACKGROUND OF THE INVENTION

Field of the Invention

The present invention concerns a control method for the screen display of a medical imaging system and a medical imaging system controlled by such a method.

Description of the Prior Art

The user-specific arrangement and structuring of image data on a screen display of a medical imaging system can only be carried out on the basis of extensive definitions on a complex technical level.

SUMMARY OF THE INVENTION

An object of the present invention is to structure image data automatically for a screen display without extensive definitions having to be carried out on a complex technical level.

According to a first aspect of the invention, the object is achieved by a control method for a screen display of a medical imaging system having the steps of operating a medical image data acquisition scanner in order to acquire an image data set of a patient and providing the acquired image data set to a computer, comparing the acquired image data set in the computer with a number of pre-stored image data sets, each of which is stored with layout parameters for the screen display associated therewith, and displaying the acquired image data set with the layout parameters associated with the pre-stored image data set that has the greatest similarity with the acquired image data set. The image data set is acquired, for example, by execution of a pulse sequence in a magnetic resonance tomography scanner or by evaluating multiple X-ray images recorded from different directions in a computed tomography scanner. The similarity is determined by a comparison of the acquired image data set with each of the individual pre-stored image data sets. The similarity can be determined, for example, by a correlation parameter or other similarity value. The set among the pre-stored image data sets that has the highest correlation parameter or similarity value with respect to the acquired image data set also has the greatest similarity to it. The technical advantage is thereby attained that a rapid, simple and transparent structuring of the image data sets can be achieved.

In an embodiment of the method, the similarity between the acquired image data set and the pre-stored image data sets is determined on the basis of DICOM attributes. This allows a similarity analysis to be achieved with a small computation effort.

In a further embodiment of the method, the similarity between the acquired image data set and the pre-stored image data sets is determined on the basis of an image analysis. This allows a similarity analysis can be achieved with a high degree of reliability.

In another embodiment of the method, the layout parameters for the acquired image data set are changeable. This allows a layout of the image data can be changed in a user-specific manner.

In a further embodiment of the method, the acquired image data set can be added, together with the associated layout parameters, to the pre-stored image data sets. This means, the pre-stored image data sets are extended by one image data set. This allows the changed layout can be used for the future representation of further image data sets.

In another embodiment of the method, the layout parameters are changeable on the screen display by a drag-and-drop action. The drag-and-drop action operates a graphical user interface of a computer by moving graphical elements with a pointing device. An element such as a pictogram can thus be dragged and dropped over a possible target. This allows the layout to be changed easily and rapidly.

In another embodiment of the method, the layout parameters control the temporal sequence of a display of the image data of the image data set on the screen display. This allows a particularly suitable sequence of the image data to be achieved.

In a further embodiment of the method, the pre-stored image data sets are provided on an external data store to which a number of medical imaging systems have access. The external data store is connected, for example, via a data network such as a cloud, for storing data in the Internet. This allows pre-knowledge of many users to be accessed in order to find a suitable layout.

In a further embodiment of the method, the layout parameters are automatically selected on the basis of a scan protocol as set. This allows the layout to also be configured without an acquired image data set.

In another embodiment of the method, a scan protocol is associated with a segment of the screen display. This allows scan protocols to be flexibly arranged in adjacent segments of the screen display.

In another embodiment of the method, the imaging medical system is a magnetic resonance tomography apparatus or a computed tomography apparatus.

According to a second aspect of the invention, the object is achieved by a medical imaging system having a medical data acquisition scanner for acquiring an image data set of a patient, a computer having a comparator that compares the acquired image data set with a number of pre-stored image data sets, each of which is stored layout parameters for the screen display associated therewith, and a display screen at which the computer causes the acquired image data set to be displayed with the layout parameters of the pre-stored image data set that has the greatest similarity to the acquired image data set. The medical imaging system achieves the same advantages as the method according to the first aspect of the invention.

According to a third aspect of the invention, the aforementioned object is achieved by a non-transitory, computer-readable data storage medium encoded with programming instructions that, when the storage medium is loaded into a computer or computer system of magnetic resonance apparatus, cause the computer or computer system to implement any or all of the embodiments of the method according to the invention, as described above.

DESCRIPTION OF THE PREFERRED EMBODIMENTS

Figure 1:
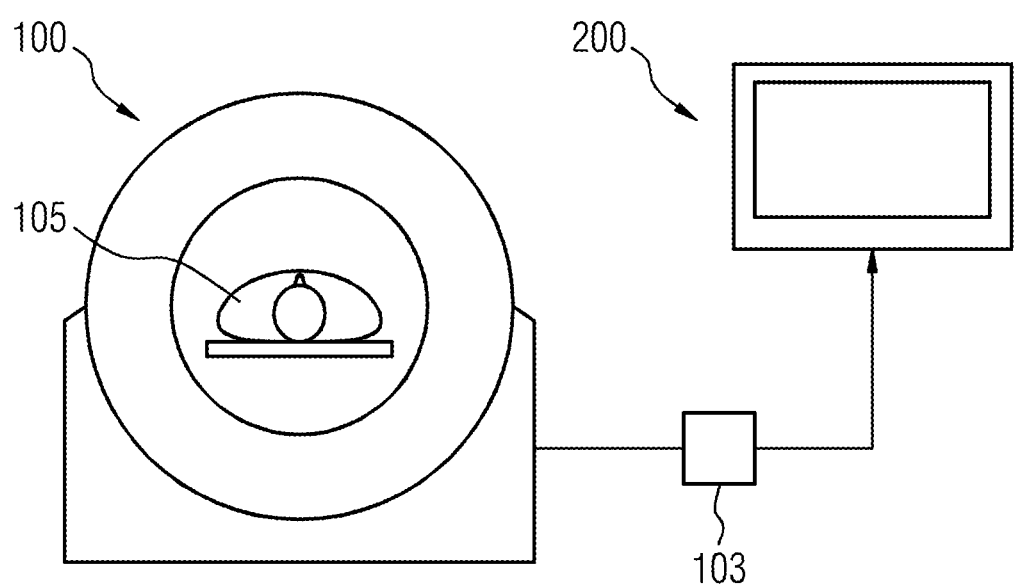
FIG. 1 shows a magnetic resonance tomography apparatus according to the invention.

FIG. 1 shows a magnetic resonance tomography apparatus 100 as an example a medical imaging system. The magnetic resonance tomography apparatus (scanner) 100 serves for the medical imaging examination of a patient 105. Magnetic resonance tomography (MRT) uses a basic magnetic field and the effect of that radiation of radio-frequency impulses has on atomic nuclei of the body tissue of the patient 105. The atoms are brought, by execution of a pulse sequence, into an excited state. As the atoms transition from the excited state into the steady state (relaxation), the atoms emit electromagnetic signals that can be registered by the magnetic resonance tomography apparatus 100 as a resonance signal.

The properties of this resonance signal depend on the pulse sequence and the body tissue from which the resonance signal is emitted. With magnetic resonance tomography, image data sets 103 of the body can be obtained that can be reconstructed as, for example, sectional images, which permit an assessment of pathological changes in the patient 105. These image data sets 103 can be displayed on a screen display 200.

Users of the magnetic resonance tomography device 100, such as radiologists, strive to ensure that the acquired image data sets 103 are displayed in a pre-determined sequence and with pre-determined layout settings on the screen display 200. The image data sets 103 thus should be arranged and represented so that the diagnosis can be made rapidly and reliably by the radiologist. However, the suitable representation and arrangement of the image data for this purpose can differ depending upon the examination region of the patient and the radiological modality.

For example, for a standard head examination, a radiologist would like an image series weighted with the relaxation time T1 (T1 image series) to be displayed in the left upper region of the screen display 200 and an image series weighted with the relaxation time T2 (T2 image series) for comparison to be displayed adjoining it in the right upper region of the screen display 200. In the case of an oncological examination of the head, however, apart from the T1 image series, a further T1 image series is to appear following a contrast medium administration and the T2 image series is to appear in the second line under the T1 image series. In another case, for a computed tomography examination, the radiologist would like to see a volume with a soft tissue window and a volume with a bone window alongside one another. The same applies for a chronologically structured logical sequence of the image data. The totality of a structured display of the image data set 103 is named a "view". The view relates both to the arrangement of the image data on the screen display 200 and also the sequence of image data on the screen display 200.

It is therefore advantageous to structure the image data sets 103 automatically for the screen display 200 without extensive definitions having to be carried out on a complex technical level.

For this purpose, following an examination, on a first reading of a case the radiologist interactively generates a structured view according to his personal conceptions on the basis of an already existing image data set 103. In this process, layout parameters are specified. The layout parameters stipulate in which way the image data set is displayed on a display. The layout parameters comprise, for example, the number of the image segments on the screen (2×2 or 3×3), an allocation of particular image series to the segments, a sequence of several layouts, a representation of image data within an image series (bone window, soft tissue window), zoom factors, synchronization settings or particular angles of view for a three-dimensional volume. The same applies for a plurality of studies on comparison with previous examinations. In general, the layout parameters can comprise all the parameters with which a particular display of the image data set 103 is controlled.

The allocation of the respective image data to image segments of the screen display 200 is based on DICOM attributes (DICOM=Digital Imaging and Communications in Medicine). The DICOM attributes are defined in the DICOM standard which is an open standard for storage and exchange of information in medical image data management. The DICOM attribute is defined via a stipulated eight-place hexadecimal number, a so-called "data tag".

The first four places of the data tag define the association of the attribute to a particular group (such as, for example, file meta-information), and the four further places determine the element. For better legibility, a DICOM data tag is normally represented in the form (xxxx, yyyy) with a comma in the middle.

In a further step, a self-learning system can additionally carry out an image analysis and intervene correctively if a DICOM value does not match a particular image value. For example, "T1" is still present in the name of the recorded pulse sequence although, on the basis of the amended image parameters, it is a T2 contrast image that is shown. This property can be read partially also from further DICOM tags in addition to the sequence name. However, for the radiologist, it is ultimately the image impression that is decisive.

The magnetic resonance tomography device 100 is configured as a self-learning (Deep Learning) system and also learns the decisive layout parameters step by step. Following an initial manual and interactive structuring of the image data set 103, the radiologist can actuate a storage button so that the image data set 103 is linked to this examination (study) with the selected layout parameters. If the radiologist loads a new study, the magnetic resonance tomography device 100 attempts, using identity and similarity rules to discover, on the basis of the image data set 103, whether there is already a pre-defined view for this examination.

If no pre-defined view is found, the magnetic resonance tomography device 100 loads a standard view. The radiologist can also manually allocate one of the pre-defined views to the image data set 103 of this study and undertake small adjustments. The magnetic resonance tomography device 100 stores these adjustments as possible variants and additionally learns to identify the new study also as a similar study.

With each new study that the radiologist assesses, the magnetic resonance tomography device 100 learns which layout parameters of a study are relevant for the allocation of particular views and which variants within a view are to be used on the individual data within a study. If a study is recognized as similar to another study which is already provided with a pre-defined view, the pre-defined view is loaded and is filled with the existing image data.

The radiologist can manually allocate into individual segments of the screen display 200 image data that cannot be automatically allocated and so can create variants of the view in the magnetic resonance tomography apparatus 100, which are all stored as belonging to a particular study type. The image data sets 103 are loaded according to the similarity principle into existing segments of the screen display 200 and provided with the corresponding attributes. The more studies that have been assessed, the more robust and reliable is an allocation to views and their detailed design.

The radiologist can inform the magnetic resonance tomography apparatus 100 by explicitly storing which settings are to be stored. In this case, the magnetic resonance tomography apparatus 100 indicates whether a new view has been created or a variant of an existing view has been generated. The radiologist can change this automated allocation and freely assign the names of the views.

In an administrative view, all the attributes, such as for example window values, zoom factors or image filters can be listed in detail and correspondingly selected or deselected. In a further configuration level for a plurality of users of a department, a variant for administrators and a further variant for regular users exist. For example, settings solely from one administrator can be taken into account and stored. Regular users, however, have no influence on the regular structure of the self-learning system. In general, the settings can be stored per system, per user or for all users in general and the system learns to distinguish different examination types.

The manual placement of layout parameters which determine the visualization of medical image data is automated by the self-learning system. Pre-defined views and automated allocations of views to radiological studies can increase the reading efficiency and the diagnostic standard. In the context of quality, radiological novices in particular, profit from the prior knowledge of experienced radiologists as to how a particular study should best be assessed. The performance in the data analysis, allocation and the speed at which the system can learn the allocations is increased by the simple level of the DICOM or header parameters. Only for a fine optimization of the allocation is an image analysis accessed. The display of the allocations made enables the user, if required, to remain with a control system and also to control the system explicitly according to his requirements.

In apparatuses such as the magnetic resonance tomography apparatus 100, there often exists a database of structured reading protocols, i.e. studies with associated workflows and layouts contained therein with allocations of image data for particular segments. These reading protocols can be fed to a self-learning system (Deep Learning) with image material respectively adapted for this purpose for radiological examinations.

By this procedure, the magnetic resonance tomography apparatus 100 can recognize which DICOM parameters or other header parameters of the image data sets 103 are relevant for the allocation of series to particular segments and for the allocation of studies to a particular reading protocol. The magnetic resonance tomography apparatus 100 can derive further patterns regarding which studies each have their own reading protocol or which main variants there are per study. Patterns can be derived via the characteristics of the individual reading protocols per study.

In addition, the actual radiological image data is transferred to the system which consequently recognizes image data and header data and can allocate it accordingly. In the event of unclear header data, the system can access an additional image analysis and thus increase the reliability of a correct allocation of image data within a read protocol.

Herein, particular image data are to be organized into particular segments, particular layouts brought into particular sequences and image data visualized within the individual segments. The visualization can take place by learning of the rules for visible image impression more reliably than via the pure analysis of header data.

When such a system is used by a radiologist for the first time, a recorded study based on rules which have been worked out by means of a prior training process can be loaded into a pre-defined reading protocol which already fulfils the expectations of the radiologist.

The system recognizes, for example, an image impression of a magnetic resonance image on use of contrast medium and arranges a magnetic resonance image without the use of contrast medium for comparison beside it. For example, the system arranges a CT image from a CT lung scan together with a CT lung window or the system windows a magnetic resonance image of a heart such that a particular heart structure is maximally represented in the image.

Additionally, the system can be trained by means of a modality-specific database of image properties. For example, there is a database of MR sequences with image material stored therefor. Together with a selection of pre-defined, particularly relevant DICOM parameters, this can represent an initial input for the self-learning system in order initially to learn which parameters lead to which image impression.

By this procedure, the existing database of radiological reading sequences can be fed to a self-learning system in order to avoid a manual configuration by the user. A structured reading increases the efficiency in the findings, reduces diagnostic errors and supports standardization.

A self-learning system that uses an existing database is efficient since during the first use of the system, the user can build upon prior knowledge from radiological practice. By this means, the efficiency is increased and the self-learning system is adapted only to the institution-specific and user-specific particularities.

Radiologists can set up a display of the image data in a pre-defined manner for diagnosing or reading. For example, for one radiologist, a head examination with a particular objective is always to be processed in the same way for reading, i.e. the same layouts with the same image data at the same sites and the same sequence of layouts which follow one another.

The stipulation of which image data are to be displayed in which segments of the screen display 200 can be achieved either directly by pulling the actual image series onto the target segment or via a complex configuration of a regular print-out directly in the target segment.

In a newly set-up system 100, however, the necessary image data are often not yet available. However, scan protocols which are used for the desired examination are available at the magnetic resonance tomography device 100. A scan protocol includes the scan parameters for the acquisition of CT and MR data, for example, pulse sequences or recording angles.

The allocation of image data to segments within the layout is therefore not only possible on the basis of the image data as such, but also on the basis of the selected scan sequences or scan protocols.

For this purpose, in the reading environment, those scan programs which are available at the respective magnetic resonance tomography apparatus 100 are provided. In a simulation, the scan sequences can be converted into the resulting image series or data rolls based thereon.

The radiologist can now select the scan sequences of the magnetic resonance tomography device 100 at the site of the actual images and pull them to the desired segment of the screen display 200. If a number of magnetic resonance tomography apparatuses 100 with different scan sequences are available, a number of results series are pulled to a segment. By this means, possible alternatives exist for a segment. The sequence in which the names have been placed determines simultaneously the sequence for a possible display and thus the priority.

If no image data have yet been acquired, the configuration of a reading protocol can thus take place on the basis of scan protocols. The reading protocol can be configured by administrators independently of the available image data sets and on the basis of the existing scan protocols.

Divergences between different magnetic resonance tomography devices can already be taken into account in advance, so that they will gradually have to be included in the configuration when corresponding image data are available.

The method can be implemented by a computer code stored on a non-transitory data storage medium, with program segments for carrying out the method steps when the computer code is executed by a computer. The computer comprises a memory for storing the computer code and a processor for executing the computer code. The computer code can be loaded into the internal data memory of the computer from the storage medium. The external data storage medium can be, for example, a CD-ROM or a USB Flash memory.

Figure 2:
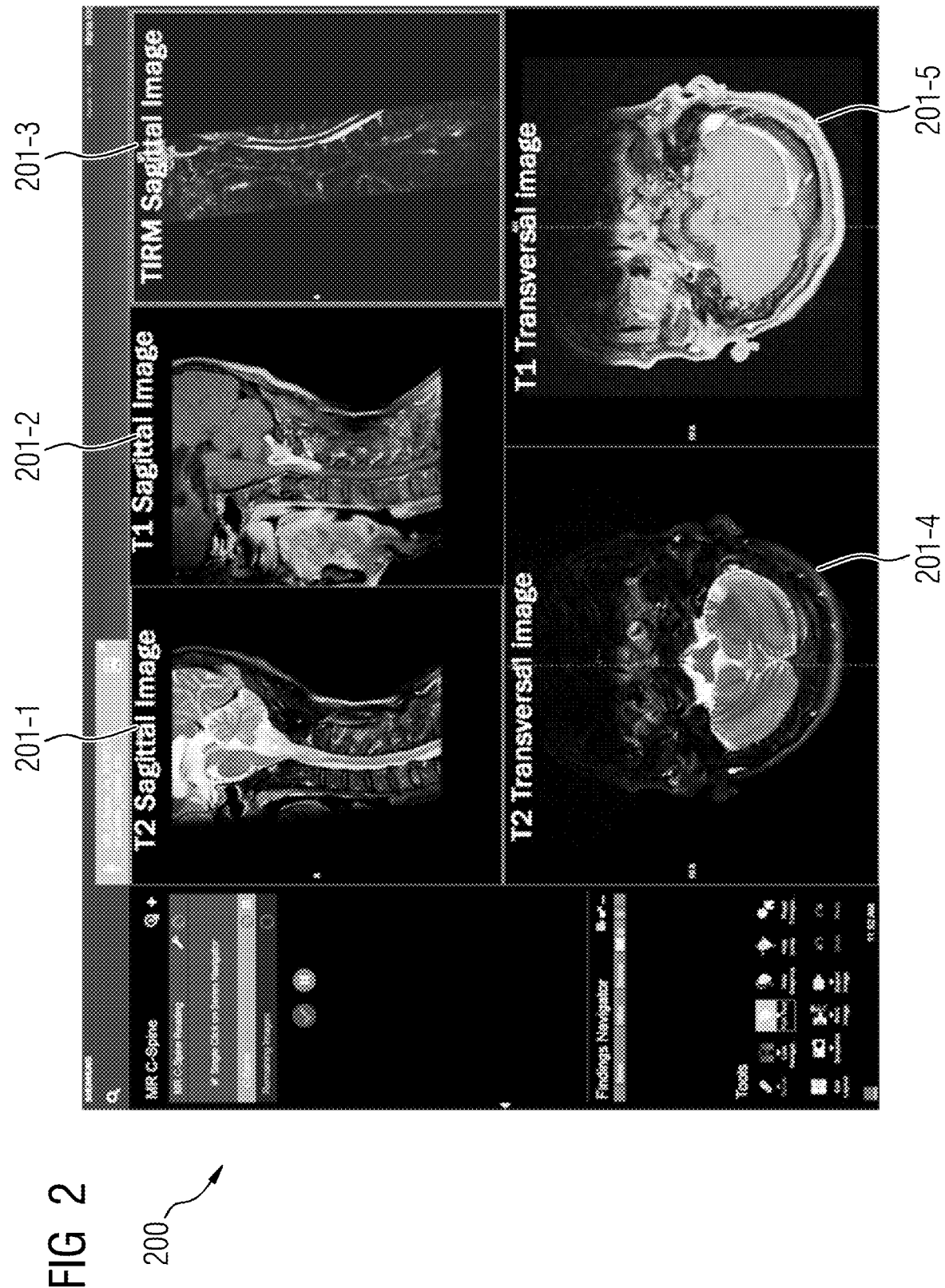
FIG. 2 shows a first view of a screen display.

FIG. 2 shows a view of the screen display 200. The screen display 200 is subdivided, for example, into different segments. The segments are formed by individual subregions of the screen display 200.

In segments 201-1, . . . , 201-5 as subregions of the screen display 200, different image data of the image data set 103 is shown. In the upper region of the screen display 200, the segments 201-1, 201-2 and 201-3 are arranged beside one another. In the lower region of the screen display 200, the segments 201-4 and 201-5 are arranged beside one another. The arrangement of the segments and the image data shown takes place on the basis of previously determined layout parameters.

Figure 3:
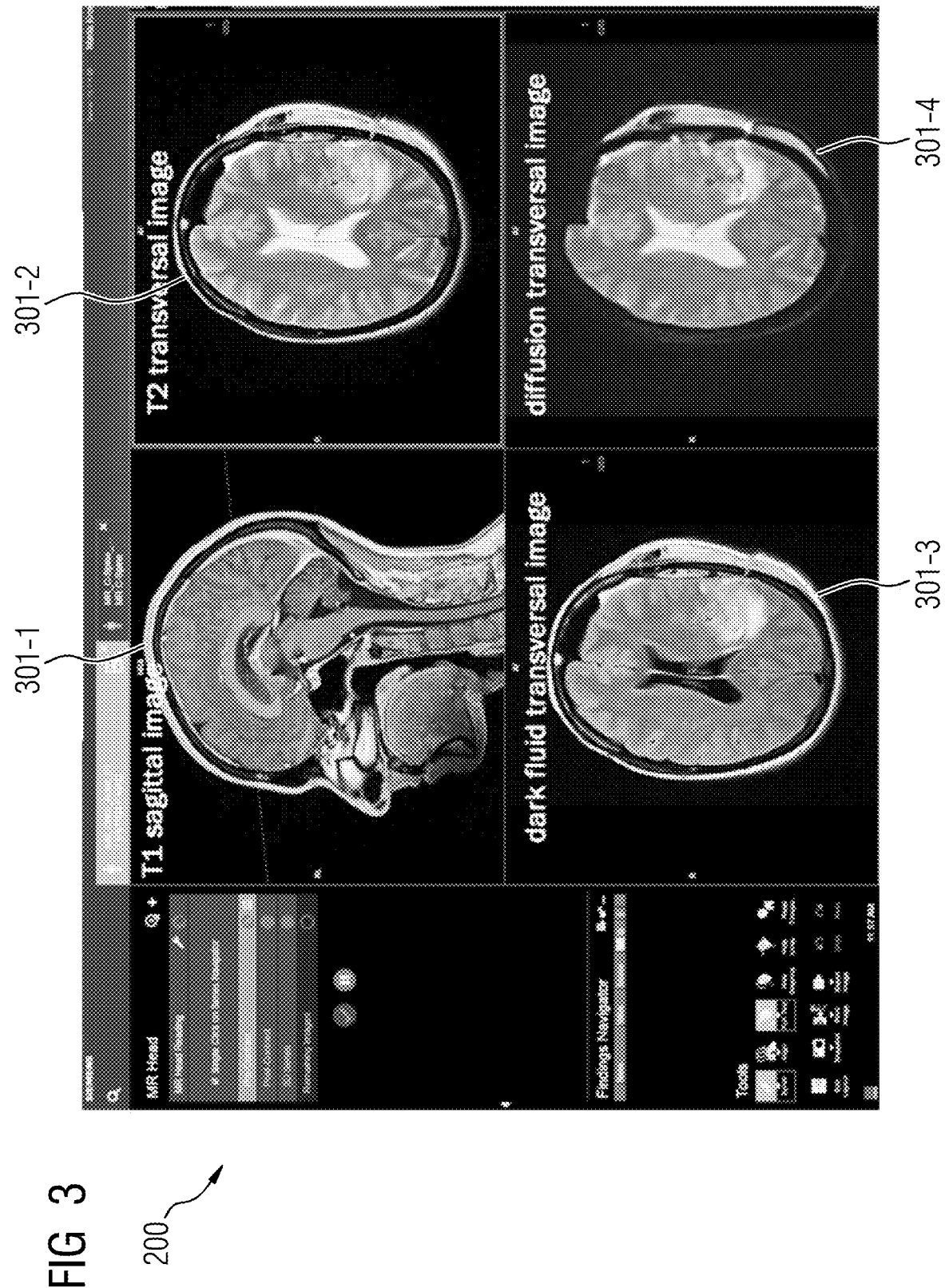
FIG. 3 shows a second view of a screen display.

FIG. 3 shows a view of the screen display 200. In segments 301-1, . . . , 301-4, different image data of the image data set 103 is shown. In the upper region of the screen display 200, the segments 301-1, and 301-2 are arranged beside one another. In the lower region of the screen display 200, the segments 301-3 and 301-4 are arranged beside one another. The arrangement of the segments and the image data shown takes place on the basis of previously determined layout parameters. These layout parameters have different values from the layout parameters for the view in FIG. 2.

Figure 4:
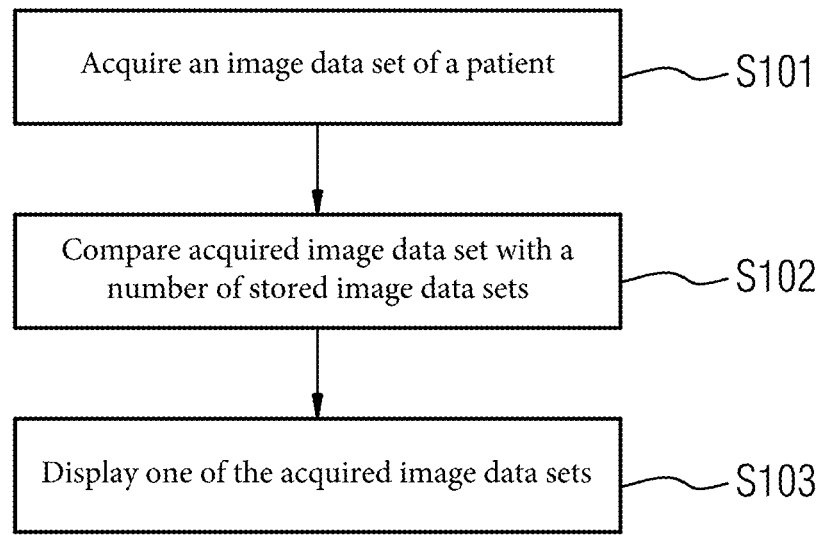
FIG. 4 is a flowchart of a method.

FIG. 4 is a block diagram of a control method for the screen display 200 of the imaging medical system 100. In step 101, firstly the image data set 103 of a patient is acquired by means of a pulse sequence. The image data set 103 comprises different image data, for example, slice images and DICOM or header attributes.

In step S102, the acquired image data set 103 is compared with a number of pre-stored image data sets to each of which layout parameters for the screen display 200 are allocated. The comparison includes, for example, a similarity analysis, a correlation analysis or a graphical image analysis.

In step S103, the acquired image data set 103 is displayed with the layout parameters of the pre-stored image data set which has the greatest similarity to the acquired image data set 103.

Figure 5:
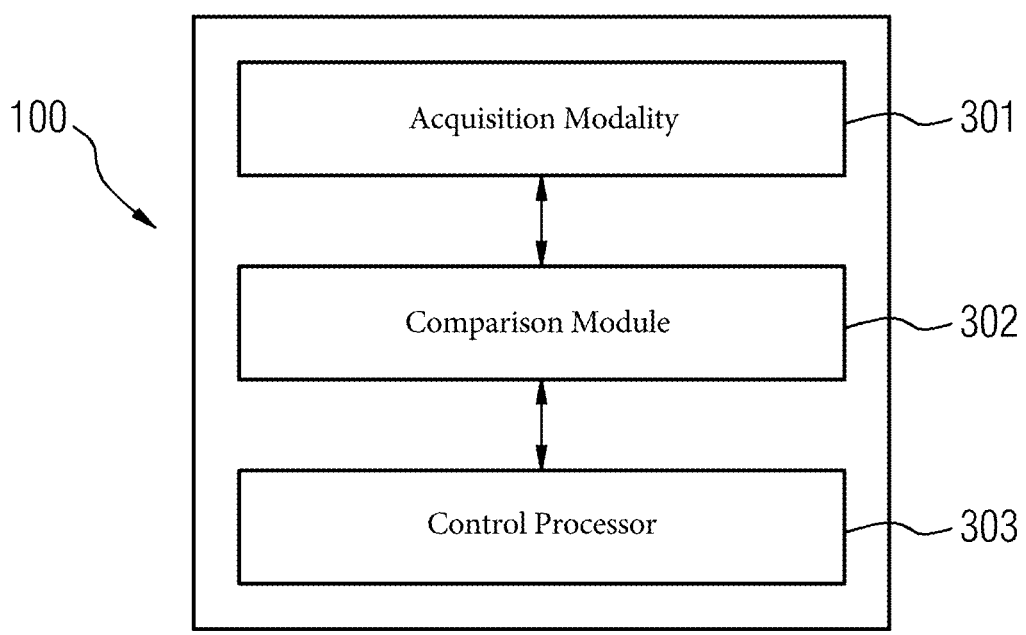
FIG. 5 is a block diagram of a medical imaging system according to the invention.

FIG. 5 shows a block diagram of a medical imaging system. The medical imaging apparatus 100 has an acquisition modality 301 for acquiring an image data set 103 of a patient, such as by execution of a pulse sequence. The acquisition modality 301 can be, for example, a magnetic resonance tomography apparatus.

A comparison module 302 serves as a comparator for comparison of the acquired image data set 103 with a number of pre-stored image data sets to each of which layout parameters for the screen display 200 are allocated. The comparison module 302 is formed, for example, by an electrical digital circuit that has a data memory for storing the image data sets and a processor for processing the image data sets. The processor is also able to carry out a similarity analysis, a correlation analysis or a graphical image analysis.

A control processor 303 serves for displaying the acquired image data set 103 on a display screen, with the layout parameters of the pre-stored image data set which has the greatest similarity to the acquired image data set 103. For this purpose, the control processor 303 has an electrical digital circuit that controls the screen display 200 on the basis of the layout parameters such that the image data set 103 is displayed in the intended layout.

All the features described and shown in conjunction with individual embodiments of the invention can be provided in different combination in the subject matter according to the invention in order simultaneously to realize the advantageous effects thereof.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A control method for presenting an acquired medical image data set at a display screen, said method comprising:
    with a computer, acquiring an image data set representing an image of a patient;
    in said computer, comparing the acquired image data set with a plurality of pre-stored image data sets, each of said pre-stored image data sets being stored with respective layout parameters associated therewith, the respective layout parameters identifying a manner in which each respective one of the pre-stored image data sets is presented on the display screen;
    in said computer, identifying one of said pre-stored image data sets having a greatest similarity to said acquired image data set based upon the act of comparing the acquired image data set with the plurality of pre-stored image data sets; and
    from said computer, presenting the acquired image data set at the display screen, which is in communication with said computer, in accordance with the layout parameters of said one of said pre-stored image data sets having said greatest similarity to the acquired image data set.

2. A control method as claimed in claim 1 comprising acquiring said image data set of the patient by operating a data acquisition scanner of a medical imaging apparatus in order to acquire measured data from the patient, and reconstructing said image data set from said measured data.

3. A control method as claimed in claim 1 comprising assigning each of said acquired image data set and each of said pre-stored image data sets respective digital imaging and communications in medicine (DICOM) attributes, and determining said greatest similarity based on said DICOM attributes.

4. A control method as claimed in claim 1 comprising determining said greatest similarity by executing an image analysis algorithm in said computer.

5. A control method as claimed in claim 1 comprising changing said layout parameters of the acquired image data set at said display screen via user interaction with said display screen.

6. A control method as claimed in claim 5 comprising changing said layout parameters using a drag-and-drop action on said display screen.

7. A control method as claimed in claim 5 comprising displaying said acquired image data set at said display screen by adding said acquired image data set on said display screen to said one of said pre-stored image data sets and the layout parameters associated with said one of said pre-stored image data sets.

8. A control method as claimed in claim 1, wherein said layout parameters control a temporal sequence of a presentation of image data in the acquired image data set at said display screen.

9. A control method as claimed in claim 1 comprising storing said plurality of pre-stored image data sets in a memory that is external to said computer, and configuring said memory to allow a plurality of different medical imaging apparatuses to access said memory.

10. A control method as claimed in claim 1 comprising selecting said layout parameters for the acquired image data set automatically based on a specified scan protocol for acquiring said acquired image data set.

11. A control method as claimed in claim 10 comprising allocating said specified scan protocol to a region of the presentation of said acquired image data set at said display screen.

12. A control method as claimed in claim 1 comprising acquiring said acquired image data set from a magnetic resonance tomography apparatus or a computed tomography apparatus.

13. A control method as claimed in claim 1, comprising determining said greatest similarity by executing an similarity analysis in said computer.

14. A control method as claimed in claim 1, comprising determining said greatest similarity by executing a correlation analysis in said computer.

15. A control method as claimed in claim 1, comprising when, in said computer, one of said pre-stored image data sets having a greatest similarity to said acquired image data set is not identified, presenting the acquired image data set at the display screen in accordance with the layout parameters of a standard view.

16. A control method as claimed in claim 15, further comprising:
modifying the layout parameters of the standard view to present the acquired image data set at the display screen in accordance with a variant of the standard view; and
adding the acquired image data presented in accordance with the presented variant to said pre-stored image data sets.

17. A control method as claimed in claim 16, further comprising:
storing which layout parameters associated with the variant of the standard view are to be stored with said pre-stored image data sets.

18. A control method as claimed in claim 1, wherein presenting the acquired image data set at the display screen in accordance with the layout parameters of said one of said pre-stored image data sets includes allocating portions of the acquired image data set to different regions of the display further based upon a selected scan sequence or scan protocol used to obtain the acquired image data.

19. A medical imaging apparatus, comprising:
a data acquisition scanner;
a computer configured to operate the data acquisition scanner in order to acquire measured data from a patient, and said computer being configured to reconstruct an image data set from said measured data;
said computer being configured to compare the acquired image data set with a plurality of pre-stored image data sets, each of said pre-stored image data sets being stored with respective layout parameters associated therewith, the respective layout parameters identifying a manner in which each respective one of the pre-stored image data sets is presented on a display screen;
said computer being configured to identify one of said pre-stored image data sets having a greatest similarity to said acquired image data set based upon the comparison of the acquired image data set with the plurality of pre-stored image data sets; and
said computer being configured to present the acquired image data set at the display screen, which is in communication with said computer, in accordance with the layout parameters of said one of said pre-stored image data sets having said greatest similarity to the acquired image data set.

20. A non-transitory, computer-readable data storage medium encoded with programming instructions, said storage medium being loaded into a computer and said programming instructions causing said computer to:
acquire an image data set representing an image of a patient;
compare the acquired image data set with a plurality of pre-stored image data sets, each of said pre-stored image data sets being stored with respective layout parameters associated therewith, the respective layout parameters identifying a manner in which each respective one of the pre-stored image data sets is presented on a display;
identify one of said pre-stored image data sets having a greatest similarity to said acquired image data set based upon the comparison of the acquired image data set with the plurality of pre-stored image data sets; and
present the acquired image data set at the display screen, which is in communication with said computer, in accordance with the layout parameters of said one of said pre-stored image data sets having said greatest similarity to the acquired image data set.

* * * * *